United States Patent [19]

Greenberg et al.

[11] 4,401,677
[45] Aug. 30, 1983

[54] ENKEPHALINASE INHIBITORS

[75] Inventors: Roland Greenberg, Princeton; David W. Cushman, West Windsor, both of N.J.; B. Richard Vogt, Yardley, Pa.; Frank L. Weisenborn, Titusville; Michael J. Antonaccio, Princeton, both of N.J.

[73] Assignee: E. R. Squibb & Sons, Inc., Princeton, N.J.

[21] Appl. No.: 310,192

[22] Filed: Oct. 9, 1981

[51] Int. Cl.³ .............................................. A61Y 31/19
[52] U.S. Cl. .................................................. 424/317
[58] Field of Search ...................................... 424/317

[56] References Cited

U.S. PATENT DOCUMENTS

| 4,053,651 | 10/1977 | Ondetti et al. | 424/319 |
| 4,235,885 | 11/1980 | Sundeen et al. | 424/177 |
| 4,254,107 | 3/1981 | Veber et al. | 424/177 |
| 4,329,495 | 5/1982 | Bindra | 562/426 |

FOREIGN PATENT DOCUMENTS 38758 10/1981 European Pat. Off. .

OTHER PUBLICATIONS

Roques et al., "The Enkephalinase Inhibitor Thiorphan . . .", Nature, vol. 288, Nov. 1980, p. 286–288.
Hughes et al., "Identification of Two Related Pentapeptides . . .", Nature, vol. 258, Dec. 1975, p. 577–579.
Malfroy et al., "High Affinity Enkephalin . . .", Nature, vol. 276, Nov. 1978, p. 523–526.
Patey et al., "Selective Protection of Methionine Enkephalin . . .", Science, vol. 212, Jun. 1981, p. 1153–1155.

Primary Examiner—Stanley J. Friedman
Attorney, Agent, or Firm—Lawrence S. Levinson; Stephen B. Davis

[57] ABSTRACT

The degradation of enkephalins in a mammalian host is inhibited by administration of an enkephalinase enzyme inhibitor of the formula

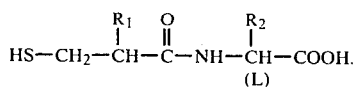

11 Claims, No Drawings

ENKEPHALINASE INHIBITORS

BACKGROUND OF THE INVENTION

Roques et al. (Nature Vol. 288, November 1980, p. 286–288) disclose that thiorphan, [(DL-3-mercapto-2-benzylpropanoyl)]-glycine, is an inhibitor of enkephalinase in vitro in nanomolar concentration and in vivo after either intracerebroventricular or systemic administration.

Ondetti et al. in U.S. Pat. No. 4,053,651 disclose that various mercaptoalkanoyl amino acids are useful hypotensive agents due to their ability to inhibit the angiotensin converting enzyme.

Sundeen et al. in U.S. Pat. No. 4,235,885 disclose that mercaptoalkanoyl amino acids of the formula $$\begin{array}{c} H_3C \quad\quad CH_3 \\ \diagdown \quad \diagup \\ CH \\ | \\ CH_2 \quad O \\ | \quad\quad \| \\ HS-CH_2-CH-C-R_2 \end{array}$$

wherein $R_2$ can be an amino acid are useful in the treatment of rheumatoid arthritis due to their mammalian collagenase inhibitory activity.

BRIEF DESCRIPTION OF THE INVENTION

This invention is directed to the discovery that enkephalinase is inhibited by compounds of the formula $$HS-CH_2-\underset{*}{\overset{R_1}{\underset{|}{CH}}}-\overset{O}{\overset{\|}{C}}-NH-\overset{(L)}{\underset{\underset{R_2}{|}}{CH}}-COOH \quad (I)$$

and salts thereof. In formula I, and throughout the specification, the symbols are as defined below.

$R_1$ is straight or branched chain alkyl of 1 to 4 carbons, benzyl, or phenethyl.

$R_2$ is straight or branched chain alkyl of 1 to 4 carbons, $-(CH_2)_n-\phi$, $-(CH_2)_n-\phi-OH$, $-(CH_2)_n-\phi(OH)_2$, $-(CH_2)_n-\text{indolyl}$, $-(CH_2)_n-\text{pyrrolyl}-N$, $-(CH_2)_n-NH_2$, $-(CH_2)_n-SH$, $-(CH_2)_n-S$-alkyl wherein alkyl is straight or branched chain of 1 to 4 carbons, $$-(CH_2)_n-NH-C\begin{array}{c}\diagup NH \\ \diagdown NH_2\end{array}, \text{ or } -(CH_2)_n-\overset{O}{\overset{\|}{C}}-NH_2.$$

n is an integer from 1 to 4.

Preferred compounds of formula I to be employed within the method of this invention are those wherein:

$R_1$ is $-CH_3$, $-CH_2-CH(CH_3)_2$, or $R_1$ is $-CH_3$, $-CH_2-CH(CH_3)_2$, or $-CH_2-\phi$, especially $-CH_2-\phi$.

$R_2$ is $-CH_3$, $-CH_2-CH(CH_3)_2$, $-CH_2-\phi$, $-CH_2-\phi-OH$, $-CH_2-\phi(OH)_2$, $-CH_2SH$, $-(CH_2)_2SCH_3$, $-(CH_2)_3NH-C\begin{array}{c}\diagup NH \\ \diagdown NH_2\end{array}$, $-(CH_2)_4NH_2$, $-CH_2-\text{pyrrolyl}-N$, $-CH_2-\text{indolyl}$, or $-CH_2-\overset{O}{\overset{\|}{C}}-NH_2$.

DETAILED DESCRIPTION OF THE INVENTION

As taught by Ondetti et al. and Sundeen et al. in the above noted patents, the compounds of formula I can be prepared by acylating an amino acid of the formula $$H_2N-\underset{\underset{R_2}{|}}{\overset{(L)}{CH}}-COOH \quad (II)$$

with an acid or its chemical equivalent of the formula $$R_3-S-CH_2-\underset{*}{\overset{R_1}{\underset{|}{CH}}}-\overset{O}{\overset{\|}{C}}-OH \quad (III)$$

wherein $R_3$ is a protecting group such as lower alkanoyl of 1 to 4 carbons, preferably acetyl, or benzoyl. The above acylation yields the intermediate of the formula $$R_3-S-CH_2-\overset{R_1}{\underset{*}{CH}}-\overset{O}{\overset{\|}{C}}-NH-\overset{(L)}{\underset{R_2}{CH}}-COOH. \quad (IV)$$

Treatment of the intermediate of formula IV by conventional hydrolysis or ammonolysis yields the mercapto compounds of formula I.

This acylation reaction can be effected in the presence of a coupling agent such as dicyclohexylcarbodiimide or the like, or the acid of formula III can be activated by formation of its mixed anhydride, symmetrical anhydride, acid halide, active ester or the use of Woodward reagent K, n-ethoxycarbonyl-2-ethoxy-1,2-dihydroquinoline or the like. For a review of the methods of acylation, see Methoden der Organischen Chemie (Houben-Weyl), Vol. XV, part II, page 1 et seq. (1974). Preferably, the acid halide, especially the acid chloride, of formula III is reacted with the amino acid or its hydrochloride salt of formula II.

The intermediate of formula IV can also be prepared by reacting the amino acid of formula II or an ester thereof with an acrylic acid or its chemical equivalent of the formula $$R_1-\underset{\underset{CH_2}{\|}}{C}-COOH \quad (V)$$

to yield, after removal of the ester group, the intermediate of the formula $$R_1-\underset{\underset{CH_2}{\|}}{C}-\overset{O}{\overset{\|}{C}}-NH-\overset{(L)}{\underset{R_2}{CH}}-COOH. \quad (VI)$$

Preferably, the acrylic acid of formula V is converted to an activated form such as the acid chloride by treatment with thionyl chloride.

The intermediate of formula VI is then treated with a thio acid of the formula (VII)

$$R_3-SH$$

to yield the intermediate of formula IV.

The compounds of formula I contain two asymmetric carbon atoms. As shown in the formulas, the asymmetric carbon in the amino acid portion of the molecule is in the L-configuration. The asymmetric carbon in the mercapalkanoyl sidechain can be in the D-, L-, or D,L-configuration. The compounds of formula I accordingly exist in stereomeric forms or as racemic mixtures thereof. All of these forms can be utilized in the method of this invention. The above described synthesis can utilize the starting compounds in the form of a racemic mixture or as a stereomer.

The compounds of formula I form basic salts with a variety of inorganic or organic bases. The pharmaceutically acceptable salts of the compounds of formula I are useful within the method of this invention. Such pharmaceutically acceptable salts include alkali metal salts such as sodium or potassium, alkaline earth metal salts such as calcium or magnesium, and salts derived from amino acids like arginine, lysine, etc. The salts are produced by reacting the acid form of the compound with an equivalent of the base supplying the desired basic ion in a medium in which the salt precipitates or in aqueous medium and then lyophilizing.

The compounds of formula I when administered to a mammalian specie are useful analgesic agents due to their enkephalinase inhibition activity. While not limiting the scope of this invention to a specific theory or mechanism of action, it has been suggested that the endogenous opiate pentapeptides, [Met[5]]-enkephalin(-Tyr-Gly-Gly-Phe-Met) and [Leu[5]]-enkephalin(Try-Gly-Gly-Phe-Leu), are neurotransmitters involved in central pain mediation (Hughes, et al., Nature, Vol. 258, December 1975, p. 577–579) and that these endogenous opiate peptides are functionally inactivated by cleavage of their Gly[3]—Phe[4] peptide bonds by a specific peptidyldipeptide hydrolase, enkephalinase, presumed to be specifically located at nerve terminals in the brain where enkephalins are released (Malfroy, et al., Nature, Vol. 276, November 1978, p. 523–526). Specific inhibitors of this enkephalinase enhance the release of endogenous enkephalins from isolated brain slices (Patey, et al., Science, Vol. 212, June 1981, p. 1153–1155) and cause analgesia in mice that is reversed by the opiate antagonist naloxone (Roques, et al., supra). In addition to analgesia, other pharmacological actions such as antitussive or antidiaharreal activities may result from prolonging the action of the body's natural opiates released from peripheral as well as central sites.

Thus, by the administration of a composition containing one or a combination of compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The compounds of formula I can be utilized as enkephalinase inhibitors for the alleviation of pain by formulating in compositions such as tablets, capsules, or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegatable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention and constitute especially preferred embodiments. All temperatures are in degrees celsius.

EXAMPLE 1

N-(DL-3-Mercapto-2-methyl-1-oxopropyl)-L-arginine

This compound is prepared as set forth in Examples 20 and 21 of U.S. Pat. No. 4,053,651 of Ondetti et al.

(a) N-(DL-3-Acetylthio-2-methyl-1-oxopropyl)-L-arginine

L-Arginine (2.61 g.) and sodium carbonate (800 mg.) are dissolved in 20 ml. of water and stirred in an ice bath. To this mixture, sodium carbonate (2.4 g.) in 10 ml. of water is added followed immediately by D,L-3-acetylthio-2-methylpropanoyl chloride which is washed in with 5 ml. of ether. The pH of the reaction mixture is about 8. The ice bath is removed and the reaction mixture is stirred for 1.5 hours at room temperature. The reaction mixture is neutralized with 50 ml. of AG-50 W-X2 resin and applied to an 80 ml. column of the same. The column is washed with water until the eluent is no longer acidic to pH paper and then with buffer pH 6.15 (900 ml. of water, 100 ml. of pyridine, 4 ml. of acetic acid). The product containing fractions are pooled and lyophilized to yield 4.1 g. of crude material. Recrystallization from methanol/ether yields 3.86 g. of N-(DL-3-acetylthio-2-methyl-1-oxopropyl)-L-arginine; m.p. 133°.

(b) N-(DL-3-Mercapto-2-methyl-1-oxopropyl)-L-arginine

N-(DL-3-Acetylthio-2-methyl-1-oxopropyl)-L-arginine (1 g.) is dissolved in a mixture of water (5 ml.) and concentrated ammonia (5 ml.). After one hour at room temperature, the pH is adjusted to 6.6 with concentrated hydrochloric acid while chilling in an ice bath. The suspension is applied to a 30 ml. column of AG-50W-X2 ion exchange resin. The column is eluted with water until no longer acidic to pH paper and then with pyridine-acetate buffer pH 6.5. The fractions containing the desired product are pooled, concentrated to dryness and lyopholized to yield 866 mg. of N-(DL-3-mercapto-2-methyl-1-oxopropyl)-L-arginine; m.p. 100°.

Anal. calc'd. for $C_{10}H_{20}N_4O_3S$: C, 44.40; H, 7.20; N, 20.23; S, 11.29. Found: C, 44.65; H, 7.58; N, 19.99; S, 10.95.

EXAMPLE 2

N-[DL-2-(Mercaptomethyl)-1-oxo-3-phenylpropyl]-L-arginine

This compound is prepared as set forth in Example 34 of Ondetti et al. U.S. Pat. No. 4,053,651.

(a) N-[DL-2-(Acetylthiomethyl)-1-oxo-3-phenylpropyl]-L-arginine

L-Arginine hydrochloride (1.85 g.) and 940 mg. of sodium carbonate are dissolved in 12 ml. of water and stirred in an ice bath. To this mixture, sodium carbonate (1.4 g.) in 6 ml. of water is added followed immediately by DL-3-acetylthio-2-benzylpropanoic acid chloride (2.25 g., Example 32 of U.S. Pat. No. 4,053,651) and washed in with 5 ml. of ether. The ice bath is removed and the pH is about 8.0. The reaction is kept at room temperature for 1.5 hours and after 30 minutes a precipitate develops. Ion exchange resin AG-50W-X2 is added until the mixture is acidic and the suspension is then applied to a 50 ml. AG-50W-X2 column. The column is washed with water until no longer acidic to pH paper and then eluted with pyridine-acetate buffer pH 6.5. The product containing fractions are pooled, concentrated to dryness, removed from benzene and absolute ethanol and dried in vacuo. The crude product is triturated with ether and filtered to yield 2.12 g. of N-[DL-2-(acetylthiomethyl)-1-oxo-3-phenylpropyl]-L-arginine.

(b) N-[DL-2-(Mercaptomethyl)-1-oxo-3-phenylpropyl]-L-arginine

N-[DL-2-(Acetylthiomethyl)-1-oxo-3-phenylpropyl]-L-arginine (1 g.) is treated with a cold solution of 2.2 ml. of water and 1.6 ml. of concentrated ammonia for one hour at room temperature. Sufficient ion exchange resin AG-50W-X2 is added to adjust the pH to 5-6 and the suspension is added to a 50 ml. AG-50W-X2 column. The column is washed with water until the eluent is no longer acidic. The column is then eluted with pyridine-acetate buffer pH 6.5 and a mixture of this buffer pH 6.5—methanol (8:2). The product containing fractions are pooled, concentrated to dryness and removed once from absolute ethanol. The crude product (403 mg.) is precipitated from methanol/ether to yield 292 mg. of N-[DL-2-(mercaptomethyl)-1-oxo-3-phenylpropyl]-L-arginine; m.p. 135°.

Anal. cal'd. for $C_{18}H_{24}N_4O_3S.H_2O$: C, 52.00; H, 7.10; N, 15.10; S, 8.65 Found: C, 52.50; H, 6.94; N, 14.97; S, 8.34.

EXAMPLE 3

N-(DL-3-Mercapto-2-methyl-1-oxopropyl)-L-tryptophan (a) N-(DL-3-Acetylthio-2-methyl-1-oxopropyl)-L-tryptophan L-Tryptophan (3.06 g.) is dissolved in 17.6 ml. of 0.85 N sodium hydroxide with stirring in an ice bath. To this solution, 7.5 ml. of 2 N sodium hydroxide is added followed immediately by DL-3-acetylthio-2-methylpropanoyl chloride (2.7 g.) and 5 ml. of ether. The ice bath is removed and the pH of the reaction mixture is between 7-8. After two hours, the reaction mixture is extracted twice with ethyl acetate, the aqueous phase is acidified with concentrated hydrochloric acid, saturated with sodium chloride and extracted with ethyl acetate to yield 4.9 g. of crude product. Purification is achieved on a 150 g. silica gel column eluting with benzene/acetic acid (7:2) to yield 2.3 g. of N-(DL-3-acetylthio-2-methyl-1-oxopropyl)-L-tryptophan.

(b) N-(DL-3-Mercapto-2-methyl-1-oxopropyl)-L-tryptophan

N-(DL-3-Acetylthio-2-methyl-1-oxopropyl)-L-tryptophan (918 mg.) is taken up in 9 ml. of methanol with stirring under an argon blanket. Concentrated $NH_4OH$ (9 ml.) is added. After 30 minutes, the methanol is removed in vacuo, the aqueous phase is acidified with solid potassium bisulfate and extracted into ethyl acetate to yield 790 mg. of N-(DL-3-mercapto-2-methyl-1-oxopropyl)-L-tryptophan.

Anal. calc'd. for $C_{15}H_{13}N_2O_3S.H_2O$: C, 55.60; H, 4.76; N, 8.65 Found: C, 56.37; H, 5.56; N, 8.81.

EXAMPLE 4

N-(DL-3-Mercapto-2-methyl-1-oxopropyl)-L-tyrosine (a) N-(DL-3-Acetylthio-2-methyl-1-oxopropyl)-L-tyrosine L-Tyrosine (2.718 g.) is suspended in 17.6 ml. of 0.85 N sodium hydroxide with stirring in an ice bath. To this mixture, 7.5 ml. of 2 N sodium hydroxide is added followed immediately by 2.7 g. of DL-3-acetylthio-2-methylpropanoyl chloride and 5 ml. of ether. After 15 minutes a precipitate forms. After 1.5 hours, 30 ml. of water are added. After 4 hours, the mixture is diluted to 300 ml. with water and extracted twice with ethyl acetate. The aqueous phase is acidified with concentrated hydrochloric acid and thoroughly extracted into ethyl acetate. The crude product (4 g.) is chromatographed on silica gel eluting with benzene/acetic acid (7:3) to give 1.6 g. of N-(DL-3-acetylthio-2-methyl-1-oxopropyl)-L-tyrosine.

(b) N-(DL-3-Mercapto-2-methyl-1-oxopropyl)-L-tyrosine

N-(DL-3-Acetylthio-2-methyl-1-oxopropyl)-L-tyrosine (1.1 g.) is taken up in methanol with stirring under an argon blanket and then treated with 10 ml. of concentrated $NH_4OH$. After 30 minutes, the methanol is removed in vacuo. The aqueous phase is taken up in ethyl acetate and acidified with 10% potassium bisulfate. The ethyl acetate mixture is washed with water, dried over $MgSO_4$ and concentrated to dryness in vacuo. Purification is achieved by silica gel column chromatography eluting with benzene/acetic acid (7:3) to yield 394 mg. of N-(DL-3-mercapto-2-methyl-1-oxopropyl)-L-tyrosine.

EXAMPLE 5

3-Hydroxy-N-(DL-3-mercapto-2-methyl-1-oxopropyl)-L-tyrosine (a) N-(DL-3-Acetylthio-2-methyl-1-oxopropyl)-3-hydroxy-L-tyrosine 3,4-Dihydroxy-L-phenylalanine (3.94 g.) is taken up in 23.6 ml. of 0.85 N sodium hydroxide with stirring in an ice bath under a blanket of argon. To this mixture, 10 ml. of 2 N sodium hydroxide is added followed immediately by 3.6 g. of DL-3-acetylthio-2-methylpropanoyl chloride in 10 ml. of ether. The ice bath is removed. After 45 minutes a precipitate comes out of solution and 30 ml. of water is added. The precipitate does not become soluble. After four hours, the reaction is acidified with concentrated hydrochloric acid while chilling and then extracted into ethyl acetate to yield 5.8 g. of crude N-(DL-3-acetylthio-2-methyl-1-oxopropyl)-3-hydroxy-L-tyrosine.

(b) 3-Hydroxy-N-(DL-3-mercapto-2-methyl-1-oxopropyl)-L-tyrosine

N-(DL-3-Acetylthio-2-methyl-1-oxopropyl)-3-hydroxy-L-tyrosine (4.9 g.) is suspended in 20 ml. of water in an ice bath under a blanket of argon. To this suspension, 20 ml. of concentrated $NH_4OH$ is added. The substrate goes into solution within four minutes. After thirty minutes at room temperature the reaction is chilled, acidified with concentrated hydrochloric acid, and extracted into ethyl acetate to yield 4.4 g. of crude product. This material is taken up in chloroform/acetic acid (7:3) and applied to 150 g. column of silica gel wrapped in aluminum foil and the fractions are worked up in a darkened laboratory. Elution is performed with chloroform/acetic acid (7:3) to yield 2.9 g. of 3-hydroxy-N-(DL-3-mercapto-2-methyl-1-oxopropyl)-L-tyrosine. A tert-butylamine salt is formed in ethyl acetate on a small aliquot.

Anal. calc'd. for $C_{13}H_{17}NO_5S.NH_2C(CH_3)_3 1.6H_2O$ C, 50.87; H, 7.38; N, 6.98; S, 7.98 Found: C, 50.94; H, 7.54; N, 6.96; S, 7.66.

EXAMPLE 6

3-Hydroxy-N-(D-3-mercapto-2-methyl-1-oxopropyl)-L-tyrosine (a) N-(D-3-Acetylthio-2-methyl-1-oxopropyl)-3-hydroxy-L-tyrosine D-3-Acetylthio-2-methylpropanoyl chloride (10.84 g.) is added in five portions to 3,4-dihydroxy-L-phenylalanine (11.83 g.) simultaneously with equal portions of 60 ml. 1 N sodium hydroxide at 0° under a nitrogen atmosphere. The additions require about one hour and the final pH is 9.0. The reaction is allowed to stir at room temperature for 4 hours. A clear solution is not obtained. The solution is layered with 200 ml. of ethyl acetate and made strongly acid with concentrated hydrochloric acid. The aqueous extract is then extracted twice with 200 ml. of ethyl acetate and the combined organic layers are dried over $MgSO_4$. The solvent is removed to yield 16 g. of crude product in the form of a tacky residue. The 16 g. residue is dissolved in 30 ml. of ethyl acetate, 250 ml. of ether are added and then 9.05 g. of dicyclohexylamine in 30 ml. of ether. A white crystalline solid forms immediately and is filtered and dried overnight to yield 14 g. of N-(D-3-acetylthio-2-methyl-1-oxopropyl)-3-hydroxy-L-tyrosine, dicyclohexylamine salt; m.p. 75°–80° (soft at 60°).

Anal. calc'd. for $C_{15}H_{19}NO_6S.C_{12}H_{21}N.2H_2O$: C, 58.07; H, 7.94; N, 5.02 Found: C, 58.29; H, 7.17; N, 4.81.

14 g. of the above dicyclohexylamine salt is converted to the free acid using ethyl acetate and potassium bisulfate. Concentration of the dried ethyl acetate solution yields 12 g. of N-(D-3-acetylthio-2-methyl-1-oxopropyl)-3-hydroxy-L-tyrosine.

(b) 3-Hydroxy-N-(D-3-mercapto-2-methyl-1-oxopropyl)-L-tyrosine

N-(D-3-Acetylthio-2-methyl-1-oxopropyl)-3-hydroxy-L-tyrosine (12.2 g.) gradually goes into solution in 60 ml. of water (ice bath and nitrogen atmosphere) and the solution is treated with 60 ml of concentrated $NH_4OH$ and stirred at room temperature under nitrogen for one hour. The solution is then layered with ethyl acetate and made strongly acidic with concentrated hydrochloric acid. The acid aqueous layer is extracted twice with 200 ml. of ethyl acetate and the combined organic layers are dried over $MgSO_4$. The solvent is removed to yield 7.5 g. of a brittle foam after drying overnight. The 7.5 g. is dissolved in 150 ml. of water, filtered and lyophilized to yield 7 g. of 3-hydroxy-N-(D-3-mercapto-2-methyl-1-oxopropyl)-L-tyrosine as a hygroscopic solid; m.p. 50°–55° (soft at 45°).

Anal. calc'd. for $C_{13}H_{17}NO_5S.0.5H_2O$: C, 50.63; H, 5.88; N, 4.54; S, 10.39 Found: C, 50.09; H, 6.06; N, 4.60; S, 10.35.

EXAMPLE 7

(±)-N$^2$-[2-(Mercaptomethyl)-4-methyl-1-oxopentyl]-L-arginine (a) (±)-N$^2$-[2-(Acetylthiomethyl)-4-methyl-1-oxopentyl]-L-arginine L-Arginine (1.9 g., 0.11 mole) is dissolved in 10 ml. of water containing sodium bicarbonate (0.9 g., 0.11 mole). This solution is cooled to 5° and 2-(acetylthiomethyl)-4-methylpentanoyl chloride (2.5 g., 0.11 mole) [prepared as set forth by Sundeen et al. in Example 2(a) of U.S. Pat. No. 4,235,885] in 5 ml. of ether is added dropwise. The pH of the reaction mixture is maintained between 7–8 by the occasional dropwise addition of saturated aqueous sodium bicarbonate. After stirring at room temperature for 5 hours, the reaction mixture is washed with ether and the aqueous solution is lyophilized overnight to yield 3.6 g. of crude product. This material is dissolved in 10 ml. of absolute ethanol and poured through a 100 ml. silica gel column (previously washed with ethanol). After 200 ml. of ethanol go through the column, product (2.3 g.) is eluted in two 50 ml. fractions. This material is chromatographed through 100 g. of Avicel using (9:1) methanol:water. Product is eluted in two 100 ml. fractions and the first fraction is lyophilized to yield 0.6 g. of analytically pure (±)-N$^2$-[2-(acetylthiomethyl)-4-methyl-1-oxopentyl]-L-arginine; softens at 64°–80°.

Anal. calc'd. for $C_{15}H_{28}N_4O_4S \cdot 0.75\ H_2O$: C, 48.18; H, 7.95; N, 14.98; S, 8.52. Found: C, 48.14; H, 7.78; N, 14.69; S, 8.58.

(b) (±)-N$^2$-[2-(Mercaptomethyl)-4-methyl-1-oxopentyl]-L-arginine (±)-N$^2$-[2-(Acetylthiomethyl)-4-methyl-1-oxopentyl]-L-arginine (0.6 g.) is dissolved in 5 ml. of water and purged with argon. To this solution, 2 ml. of 37% aqueous NH$_4$OH is added and stirred at room temperature for 2 hours. It is lyophilized overnight and the resulting white solid is washed with 60 ml. of acetonitrile containing 6 drops of water. The granular solid is filtered and dried in vacuo at 60° for 2 hours to yield (±)-N$^2$-[2-(mercaptomethyl)-4-methyl-1-oxopentyl]-L-arginine, softens at 127°.

Anal. calc'd. for $C_{13}H_{26}N_4O_3S \cdot H_2O$: C, 46.41; H, 8.39; N, 16.65; S, 9.53 Found: C, 46.38; H, 8.21; N, 16.38; S, 9.42.

EXAMPLE 8

(±)-N-[2-(Mercaptomethyl)-1-oxo-3-phenylpropyl]-L-leucine, ammonium salt (a) 2-Phenylmethyl-2-propenoyl chloride Benzyl malonic acid (13 g., 0.067 mole) is mixed with 40% aqueous dimethylamine (7.6 g., 0.068 mole) and 37% formalin (5.4 g., 0.068 mole) in 150 ml. of water. The voluminous solid which forms in 15 minutes is filtered after two hours, washed with water and dried partially in air to give 20.8 g. of benzyl malonic acid dimethylamine.

This solid is melted in a 170° oil bath and heated for 10 minutes until amine evolution stops and bubbling virtually ceases. The cooled product, a mobile liquid, is acidified with 10% potassium bisulfate, extracted with hexane, dried (Na$_2$SO$_4$) and evaporated to give 6.3 g. of solid 2-benzylacrylic acid.

The 2-benzylacrylic acid (6.0 g.) is dissolved in ether and 10 ml. of thionyl chloride are added dropwise. Reaction temperature is allowed to rise to 35°. After stirring for 2 hours, the mixture is concentrated in vacuo to yield 6.4 g. of crude 2-phenylmethyl-2-propenoyl chloride.

(b) N-(2-Methylene-1-oxo-3-phenylpropyl)-L-leucine, methyl ester

L-Leucine, methyl ester, hydrochloride (2.72 g.) is dissolved in 70 ml. of dichloromethane. Triethylamine (3.03 g.) is added, followed by the dropwise addition of 2-phenylmethyl-2-propenoyl chloride (6.4 g.) at 0°. After the reaction is stirred for 3 hours, it is diluted with 100 ml. of dichloromethane and washed sequentially with 10% aqueous hydrochloric acid, aqueous sodium bicarbonate, and water. The organic phase is dried (MgSO$_4$), filtered, and concentrated in vacuo to yield 4.4 g. of N-(2-methylene-1-oxo-3-phenylpropyl)-L-leucine, methyl ester; m.p. 67°–71°.

(c) N-(2-Methylene-1-oxo-3-phenylpropyl)-L-leucine

The methyl ester product from part (b) is dissolved in 150 ml. of methanol. Sodium hydroxide (0.8 g.) in 150 ml. of water is added dropwise and the reaction mixture is heated at 60° for 30 minutes. The reaction mixture is concentrated in vacuo to remove the methanol and then diluted with 50 ml. more of water. The aqueous phase is washed with ether and then acidified with 10% aqueous hydrochloric acid. The product is extracted with two 200 ml. portions of dichloromethane, dried (MgSO$_4$), filtered, and concentrated in vacuo to yield 4.2 g. of N-(2-methylene-1-oxo-3-phenylpropyl)-L-leucine; m.p. 56°–60°.

(d) (±)-N-[2-(Acetylthiomethyl)-1-oxo-3-phenylpropyl]-L-leucine

The N-(2-methylene-1-oxo-3-phenylpropyl)-L-leucine (4.2 g.) is dissolved in 50 ml. of chloroform and 5 ml. of thiol acetic acid. This mixture is stirred under nitrogen overnight and then concentrated in vacuo to yield an almost colorless oil which slowly crystallizes out of ether to yield 2.4 g. of (±)-N-[2-(acetylthiomethyl)-1-oxo-3-phenylpropyl]-L-leucine; m.p. 90°–92°.

Anal. calc'd. for $C_{18}H_{24}NSO_4$ C, 61.51; H, 7.17; N, 3.99; S, 9.12 Found: C, 61.50; H, 7.21; N, 4.02; S, 9.06.

(e) (±)-N-[2-(Mercaptomethyl)-1-oxo-3-phenylpropyl]-L-leucine, ammonium salt (±)-N-[2-(acetylthiomethyl)-1-oxo-3-phenylpropyl]-L-leucine (1.0 g.) is suspended in 50 ml. of distilled water which is purged with argon. To this suspension is added 2 ml. of 37% NH$_4$OH and the reaction mixture is stirred under argon for 2 hours. It is lyophilized overnight to yield a white solid. This solid is stirred with 50 ml. of acetonitrile for 2 hours, filtered, and dried in vacuo for 12 hours to give 0.7 g. of (±)-N-[2-(mercaptomethyl)-1-oxo-3-phenylpropyl]-L-leucine, ammonium salt; m.p. 102°–115° with evolution of ammonia.

Anal. calc'd. for $C_{16}H_{26}N_2O_3S$ C, 58.87; H, 8.03; N, 8.58; S, 9.82 Found: C, 58.70; H, 7.96; N, 8.24; S, 9.47.

EXAMPLES 9–22

Following the procedure of Examples 1 to 7 but employing the acid chloride shown in Col. I and the amino acid shown in Col. II the intermediate shown in Col. III is obtained. Removal of the R$_3$ protecting group yields the compound shown in Col. IV which is useful in the method of treatment of this invention.

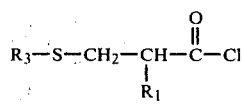

Col. I

-continued $$H_2N-\overset{(L)}{\underset{R_2}{CH}}-COOH \quad \text{Col. II}$$

$$R_3-S-CH_2-\underset{R_1}{\overset{R_1}{CH}}-\overset{O}{\overset{\|}{C}}-NH-\underset{R_2}{\overset{(L)}{CH}}-COOH \quad \text{Col. III}$$

$$HS-CH_2-\underset{}{\overset{R_1}{\underset{|}{CH}}}-\overset{O}{\overset{\|}{C}}-NH-\underset{R_2}{\overset{(L)}{CH}}-COOH \quad \text{Col. IV}$$

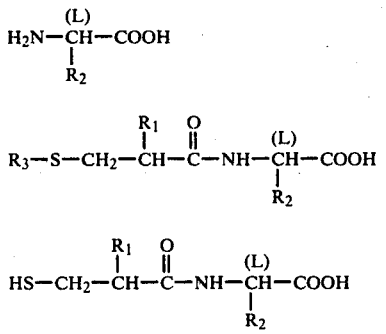

-continued

| Example | R3 | R2 | R1 |
|---|---|---|---|
| 21 | H3C—C(=O)—, H3C— | H3C—(CH2)2— | —CH2—⟨phenyl⟩—OH |
| 22 | H3C—C(=O)—, H3C— | H3C— | —CH2—CH(CH3)2 |

EXAMPLE 23

The following experiment demonstrated the ability of the compounds of formula I to inhibit the cleavage of [$^3$H-Tyr$^1$, Leu$^5$]-enkephalin by enkephalinase purified from membrane fractions of sheep corpus striatum.

Frozen sheep striatia were homogenized in 20 volumes of 50 mM Tris (i.e., 2-amino-2-hydroxymethyl-1,3-propanediol)-hydrochloric acid buffer, pH 7.7, and centrifuged at 37,000×g. for 15 minutes. The sedimented material (membrane fraction), after being washed three times by resuspension and recentrifugation, was solubilized by stirring with half the original volume of 50 mM Tris-hydrochloric acid buffer, pH 7.7, containing 1% Triton X-100 (i.e., polyethylene glycol p-isooctylphenyl ether) nonionic detergent, followed by centrifugation for 2 hours at 37,000×g. The supernatant solution (solubilized enzyme) was applied to a 1.5×30 cm—column of Whatman DE52-cellulose, previously equilibrated with the same buffer-detergent mixture. Protein was eluted from the column with a one liter gradient of 0–0.4 M sodium chloride in the same buffer mixture, with 8.7 ml. fractions being collected. Enkephalinase activity in fractions 10 to 17 was pooled, concentrated, and applied to a 2.5×80 cm. column of Sephadex G-200 equilibrated with 50 mM Tris-hydrochloric acid, pH 7.0, containing 1% polysorbate 80 detergent. The enkephalinase activity emerging as a single peak from Sephadex G-200 was used to test for inhibition activity.

Activity of the enzyme for purification and inhibitor studies was determined by the following radiochromatographic method. An assay incubation mixture of 0.02 ml. containing 70 nM [$^3$H-Tyr$^1$, Leu$^5$]-enkephalin (50,000 cpm), an appropriate dilution of the enzyme, and the inhibitor in a final concentration of 125 mM Tris-hydrochloric acid, pH 7.0, was incubated for 15 minutes at 37° before stopping the enzymatic reaction with 0.005 ml. of 1 N hydrochloric acid. An aliquot of 0.01 ml. of acidified reaction mixture was spotted onto a Whatman LK 50 silica gel thin-layer chromatography plate along with the appropriate peptide standards. After development of the plate in a solvent composed of isopropanol:ethyl acetate:5% acetic acid (2:2:1), the spots corresponding to Tyr, Tyr-Gly, Tyr-Gly-Gly, and unreacted enkephalin (Tyr-Gly-Gly-Phe-Leu), as visualized with ninhydrin reaction, were scraped from the plate, and the incorporated radioactivity was counted in a liquid scintillation counter. A comparison of the amount of $^3$H-labelled Tyr-Gly-Gly formed by uninhibited enzyme with that formed in the presence of various concentrations of an inhibitory compound allows calculation of the $I_{50}$ value, i.e., the concentration of test compound producing 50% inhibition of the enzyme under the conditions described above.

| Compound | IC$_{50}$nM |
|---|---|
| N—(DL-3-Mercapto-2-methyl-1-oxopropyl)-L-arginine (Ex. 1) | 150 |
| N—[DL-2-(Mercaptomethyl)-1-oxo-3-phenylpropyl]-L-arginine (Ex. 2) | 85 |
| N—(DL-3-Mercapto-2-methyl-1-oxopropyl)-L-tryptophan (Ex. 3) | 5 |
| N—(DL-3-Mercapto-2-methyl-1-oxopropyl)-L-tyrosine (Ex. 4) | 2.5 |
| 3-Hydroxy-N—(D,L-3-mercapto-2-methyl-1-oxopropyl)-L-tyrosine (Ex. 5) | 5 |
| 3-Hydroxy-N—(D-3-mercapto-2-methyl-1-oxopropyl)-L-tyrosine (Ex. 6) | 2.5 |
| (±)-N$^2$—[2-(Mercaptomethyl)-4-methyl-1-oxopentyl]-L-arginine (Ex. 7) | 30 |
| (±)-N—[2-(Mercaptomethyl)-1-oxo-3-phenylpropyl]-L-leucine, ammonium salt (Ex. 8) | 3 |

EXAMPLE 24

1000 tablets each containing 100 mg. of 3-hydroxy-N-(D-3-mercapto-2-methyl-1-oxopropyl)-L-tyrosine are produced from the following ingredients:

| | |
|---|---|
| 3-Hydroxy-N—(D-3-mercapto-2-methyl-1-oxopropyl)-L-tyrosine | 100 g. |
| Corn starch | 50 g. |
| Gelatin | 7.5 g. |
| Avicel (Microcrystalline cellulose) | 25 g. |
| Magnesium stearate | 2.5 g. |

The 3-hydroxy-N-(D-3-mercapto-2-methyl-1-oxopropyl)-L-tyrosine and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 mg. of active ingredient.

The compounds of Examples 1 to 5 and 7 to 22 can be formulated in a similar manner.

What is claimed is:

1. A method of inhibiting the degradation of enkephalins by the enkephalinase enzyme in a mammalian host which comprises administering to said mammal an enkephalinase inhibiting effective amount of the enkephalinase inhibitor of the formula $$\text{HS}-\text{CH}_2-\overset{R_1}{\underset{|}{\text{CH}}}-\overset{O}{\underset{\|}{\text{C}}}-\text{NH}-\overset{R_2}{\underset{|}{\text{CH}}}-\text{COOH}$$
(L)

or a pharmaceutically acceptable salt thereof wherein:
R$_1$ is straight or branched chain alkyl of 1 to 4 carbons, benzyl or phenethyl;
R$_2$ is straight or branched chain alkyl of 1 to 4 carbons,

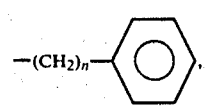,

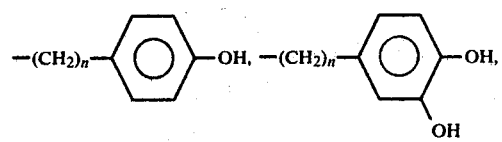

—(CH$_2$)$_n$—NH$_2$, —(CH$_2$)$_n$—SH, —(CH$_2$)$_n$—S-lower alkyl wherein lower alkyl is straight or branched chain of 1 to 4 carbons,

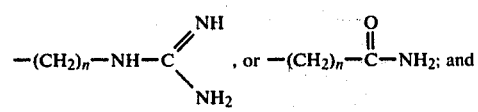

and
n is an integer from 1 to 4.

2. A method of claim 1 wherein
R$_1$ is —CH$_3$, —CH$_2$—CH(CH$_3$)$_2$, or

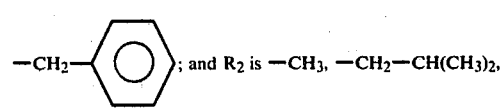; and R$_2$ is —CH$_3$, —CH$_2$—CH(CH$_3$)$_2$,

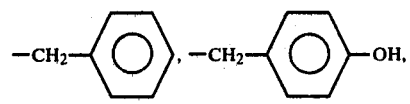,

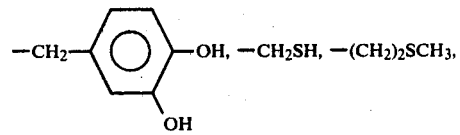

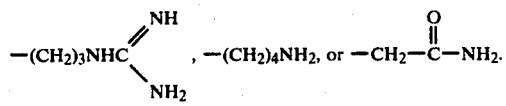

3. A method of claim 2 wherein R$_1$ is

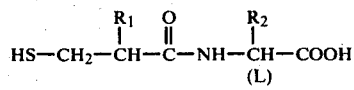

4. The method of claim 3 wherein R$_2$ is

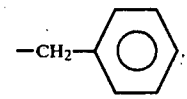

5. The method of claim 3 wherein R$_2$ is —CH$_2$—CH(CH$_3$)$_2$.

6. The method of claim 2 wherein R$_1$ is —CH$_3$ and R$_2$ is

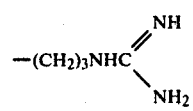

7. The method of claim 2 wherein $R_1$ is —$CH_3$ and $R_2$ is

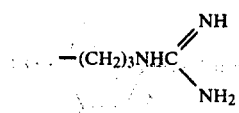

8. The method of claim 2 wherein $R_1$ is —$CH_3$ and $R_2$ is

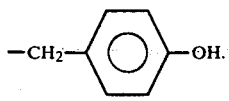

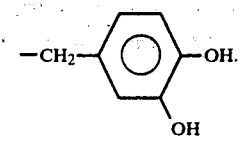

9. The method of claim 8 wherein said enkephalinase inhibitor is 3-hydroxy-N-(DL-3-mercapto-2-methyl-1-oxopropyl)-L-tyrosine.

10. The method of claim 8 wherein said enkephalinase inhibitor is 3-hydroxy-N-(D-3-mercapto-2-methyl-1-oxopropyl)-L-tyrosine.

11. The method of claim 2 wherein $R_1$ is —$CH_2$—$CH(CH_3)_2$ and $R_2$ is

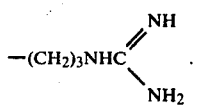

* * * * *

UNITED STATES PATENT AND TRADEMARK OFFICE
CERTIFICATE OF CORRECTION

PATENT NO. : 4,401,677

DATED : August 30, 1983

INVENTOR(S) : Roland Greenberg et al.

It is certified that error appears in the above–identified patent and that said Letters Patent are hereby corrected as shown below:

Column 2, line 14, delete "$R_1$ is $-CH_3$, $-CH_2-CH(CH_3)_2$, or" .

Signed and Sealed this

Fourteenth Day of October, 1986

[SEAL]

Attest:

DONALD J. QUIGG

Attesting Officer

Commissioner of Patents and Trademarks